(12) United States Patent
Levi et al.

(10) Patent No.: US 12,295,833 B2
(45) Date of Patent: May 13, 2025

(54) METHOD OF ASSEMBLING A PROSTHETIC HEART VALVE

(71) Applicant: Edwards Lifesciences Corporation, Irvine, CA (US)

(72) Inventors: Tamir S. Levi, Zikhron Yaakov (IL); Elena Sherman, Pardes Hana (IL); Noam Nir, Pardes-Hanna (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 792 days.

(21) Appl. No.: 17/496,670

(22) Filed: Oct. 7, 2021

(65) Prior Publication Data

US 2022/0023036 A1 Jan. 27, 2022

Related U.S. Application Data

(63) Continuation of application No. PCT/US2020/026368, filed on Apr. 2, 2020.
(Continued)

(51) Int. Cl.
*A61F 2/24* (2006.01)

(52) U.S. Cl.
CPC .......... *A61F 2/2409* (2013.01); *A61F 2/2418* (2013.01); *A61F 2220/0075* (2013.01)

(58) Field of Classification Search
CPC ................ A61F 2/2409; A61F 2/2418; A61F 2220/0075; A61F 2/24; A61F 2250/0069
See application file for complete search history.

(56) References Cited

U.S. PATENT DOCUMENTS

| 3,409,013 A | 11/1968 | Berry |
| 3,548,417 A | 12/1970 | Kisher |

(Continued)

FOREIGN PATENT DOCUMENTS

| DE | 0144167 C | 9/1903 |
| DE | 2246526 A1 | 3/1973 |

(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 3. pp. 704-708. 1992.

(Continued)

*Primary Examiner* — Leslie A Lopez
*Assistant Examiner* — Kia Xiong White
(74) *Attorney, Agent, or Firm* — Klarquist Sparkman, LLP; Joel B. German (57) ABSTRACT

A method of assembling a prosthetic heart valve comprises securing a suture loop having at least first and second windings to an outflow edge portion of an inner skirt. The first and second windings are arranged in a repeating pattern of figure-eight shape curves and each winding has a plurality of first sections attached to the outflow edge portion of the inner skirt and a plurality of second sections unattached to the inner skirt. The inner skirt is placed inside of an annular frame and the second sections of the first and second windings are placed over apices of an outflow end of the frame such that the second sections of the first and second windings reside outside of the frame. The second sections of the windings are inserted inwardly through openings in the frame and attached to selected locations on the inner skirt.

20 Claims, 5 Drawing Sheets

Related U.S. Application Data (60) Provisional application No. 62/832,402, filed on Apr. 11, 2019.

(56) References Cited

U.S. PATENT DOCUMENTS

| | | |
|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |

(56) References Cited

U.S. PATENT DOCUMENTS

| | | | |
|---|---|---|---|
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul, Jr. et al. |
| 8,167,932 B2 | 5/2012 | Bourang et al. |
| 8,291,570 B2 | 10/2012 | Fidenschink et al. |
| 8,348,998 B2 | 1/2013 | Pintor et al. |
| 8,449,606 B2 | 5/2013 | Eliasen et al. |
| 8,454,685 B2 | 6/2013 | Hariton et al. |
| 8,652,203 B2 | 2/2014 | Quadri et al. |
| 8,685,055 B2 | 4/2014 | VanTassel et al. |
| 8,747,463 B2 | 6/2014 | Fogarty et al. |
| 9,078,781 B2 | 7/2015 | Ryan et al. |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0143390 A1 | 10/2002 | Ishii |
| 2002/0173842 A1 | 11/2002 | Buchanan |
| 2003/0014105 A1 | 1/2003 | Cao |
| 2003/0040791 A1 | 2/2003 | Oktay |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0024452 A1 | 2/2004 | Kruse et al. |
| 2004/0039436 A1 | 2/2004 | Spenser et al. |
| 2004/0078074 A1 | 4/2004 | Anderson et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0010285 A1 | 1/2005 | Lambrecht et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Cali et al. |
| 2005/0137686 A1 | 6/2005 | Salahieh et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0118826 A1 | 5/2009 | Khaghani |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0004735 A1 | 1/2010 | Yang et al. |
| 2010/0049313 A1 | 2/2010 | Alon et al. |
| 2010/0082094 A1 | 4/2010 | Quadri et al. |
| 2010/0100176 A1 | 4/2010 | Elizondo et al. |
| 2010/0168844 A1 | 7/2010 | Toomes et al. |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2011/0015729 A1 | 1/2011 | Jimenez et al. |
| 2011/0022157 A1 | 1/2011 | Essinger et al. |
| 2011/0066224 A1 | 3/2011 | White |
| 2011/0137397 A1 | 6/2011 | Chau et al. |
| 2011/0218619 A1 | 9/2011 | Benichou et al. |
| 2011/0319991 A1 | 12/2011 | Hariton et al. |
| 2012/0030090 A1 | 2/2012 | Johnston et al. |
| 2012/0089223 A1 | 4/2012 | Nguyen et al. |
| 2012/0101571 A1 | 4/2012 | Thambar et al. |
| 2012/0123529 A1 | 5/2012 | Evi et al. |
| 2012/0259409 A1 | 10/2012 | Nguyen et al. |
| 2013/0023985 A1 | 1/2013 | Khairkhahan et al. |
| 2013/0046373 A1 | 2/2013 | Cartledge et al. |
| 2013/0150956 A1 | 6/2013 | Yohanan et al. |
| 2013/0166017 A1 | 6/2013 | Cartledge et al. |
| 2013/0190857 A1 | 7/2013 | Mitra et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0277563 A1 | 9/2014 | White |
| 2014/0296962 A1 | 10/2014 | Cartledge et al. |
| 2014/0330372 A1 | 11/2014 | Weston et al. |
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2015/0135506 A1 | 5/2015 | White |
| 2015/0157455 A1 | 6/2015 | Hoang et al. |
| 2016/0374802 A1 | 12/2016 | Levi et al. |
| 2017/0014229 A1 | 1/2017 | Nguyen-Thien-Nhon et al. |
| 2017/0231761 A1* | 8/2017 | Cohen-Tzemach .......... A61F 2/2418 623/2.18 |
| 2018/0028310 A1 | 2/2018 | Gurovich et al. |
| 2018/0153689 A1 | 6/2018 | Maimon et al. |
| 2018/0325665 A1 | 11/2018 | Gurovich et al. |
| 2018/0344456 A1 | 12/2018 | Barash et al. |
| 2019/0159894 A1 | 5/2019 | Levi et al. |

(56) References Cited

U.S. PATENT DOCUMENTS

| | | |
|---|---|---|
| 2019/0192288 A1 | 6/2019 | Levi et al. |
| 2019/0192289 A1 | 6/2019 | Levi et al. |

FOREIGN PATENT DOCUMENTS

| | | | |
|---|---|---|---|
| DE | 19532846 A1 | 3/1997 | |
| DE | 19546692 A1 | 6/1997 | |
| DE | 19857887 A1 | 7/2000 | |
| DE | 19907646 A1 | 8/2000 | |
| DE | 10049812 A1 | 4/2002 | |
| DE | 10049813 C1 | 4/2002 | |
| DE | 10049814 A1 | 4/2002 | |
| DE | 10049815 A1 | 4/2002 | |
| EP | 0051451 A2 * | 5/1982 | ........... A61F 2/2418 |
| EP | 0103546 A1 | 3/1984 | |
| EP | 0850607 A1 | 7/1998 | |
| EP | 1057460 A1 | 12/2000 | |
| EP | 1088529 A2 | 4/2001 | |
| EP | 1570809 A1 | 9/2005 | |
| FR | 2788217 A1 | 7/2000 | |
| FR | 2815844 A1 | 5/2002 | |
| GB | 2056023 A | 3/1981 | |
| SU | 1271508 A1 | 11/1986 | |
| WO | 9117720 A1 | 11/1991 | |
| WO | 9217118 A1 | 10/1992 | |
| WO | 9301768 A1 | 2/1993 | |
| WO | 9724080 A1 | 7/1997 | |
| WO | 9829057 A1 | 7/1998 | |
| WO | 9930646 A1 | 6/1999 | |
| WO | 9933414 A1 | 7/1999 | |
| WO | 9940964 A1 | 8/1999 | |
| WO | 9947075 A1 | 9/1999 | |
| WO | 0018333 A1 | 4/2000 | |
| WO | 0041652 A1 | 7/2000 | |
| WO | 0135878 A2 | 5/2001 | |
| WO | 0149213 A2 | 7/2001 | |
| WO | 0154624 A1 | 8/2001 | |
| WO | 0154625 A1 | 8/2001 | |
| WO | 0162189 A1 | 8/2001 | |
| WO | 0047139 A9 | 9/2001 | |
| WO | 0164137 A1 | 9/2001 | |
| WO | 0176510 A2 | 10/2001 | |
| WO | 0222054 | 3/2002 | |
| WO | 0236048 A1 | 5/2002 | |
| WO | 0241789 A2 | 5/2002 | |
| WO | 0243620 A1 | 6/2002 | |
| WO | 0247575 A2 | 6/2002 | |
| WO | 0249540 A2 | 6/2002 | |
| WO | 03047468 | 6/2003 | |
| WO | 2005034812 A1 | 4/2005 | |
| WO | 2005055883 A1 | 6/2005 | |
| WO | 2005084595 A1 | 9/2005 | |
| WO | 2006014233 A2 | 2/2006 | |
| WO | 2006032051 A2 | 3/2006 | |
| WO | 2006034008 A2 | 3/2006 | |
| WO | 2006111391 A1 | 10/2006 | |
| WO | 2006127089 A1 | 11/2006 | |
| WO | 2006138173 A2 | 12/2006 | |
| WO | 2005102015 A3 | 4/2007 | |
| WO | 2007047488 A2 | 4/2007 | |
| WO | 2007067942 A1 | 6/2007 | |
| WO | 2007097983 A2 | 8/2007 | |
| WO | 2008005405 A2 | 1/2008 | |
| WO | 2008015257 A2 | 2/2008 | |
| WO | 2008035337 A2 | 3/2008 | |
| WO | 2008091515 A2 | 7/2008 | |
| WO | 2008147964 A1 | 12/2008 | |
| WO | 2008150529 A1 | 12/2008 | |
| WO | 2009033469 A1 | 3/2009 | |
| WO | 2009042196 A2 | 4/2009 | |
| WO | 2009053497 A1 | 4/2009 | |
| WO | 2009061389 A2 | 5/2009 | |
| WO | 2009094188 A2 | 7/2009 | |
| WO | 2009116041 A2 | 9/2009 | |
| WO | 2009149462 A2 | 12/2009 | |
| WO | 2010011699 A2 | 1/2010 | |
| WO | 2010121076 A2 | 10/2010 | |
| WO | 2013106585 A1 | 7/2013 | |
| WO | 2015085218 A1 | 6/2015 | |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: In vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.

Fontaine, M.D., Arthur B., et al., "Vascular Stent Prototype; Results of Preclinical Evaluation", p. 29-34; Technical Developments and Instrumentation; Jan.-Feb. 1996, vol. 7, No. 1.

Fontaine, M.D., Arthur B., et al., "Prototype Stent: Invivo Swine Studies in the Biliary System1", p. 101-105, Journal of Vascular and Interventional Radiology; Jan.-Feb. 1997; vol. 8, No. 1.

Patrick W. Serruys, Nicolo Piazza, Alain Cribier, John Webb, Jean-Claude Laborde, Peter de Jaegere, "Transcatheter Aortic Valve Implantation: Tips and Tricks to Avoid Failure"; we file the table of contents and pp. 18 to 39 (Chapter 2) and pp. 102-114 (Chapter 8); the publication date according to the "Library of Congress Cataloging-in-Publication Data" is Nov. 24, 2009.

* cited by examiner

METHOD OF ASSEMBLING A PROSTHETIC HEART VALVE

CROSS-REFERENCE TO RELATED APPLICATIONS

The present application is a continuation of International Application No. PCT/US2020/026368, filed Apr. 2, 2020, which claims the benefit of U.S. Provisional Application No. 62/832,402, filed Apr. 11, 2019, both of which applications are incorporated herein by reference.

FIELD

The present disclosure concerns embodiments of a prosthetic valve for implantation into body ducts, such as native heart valve annuluses, and methods assembling a prosthetic heart valve.

BACKGROUND

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans.

Various surgical techniques may be used to replace or repair a diseased or damaged valve. Due to stenosis and other heart valve diseases, thousands of patients undergo surgery each year wherein the defective native heart valve is replaced by a prosthetic valve. Another less drastic method for treating defective valves is through repair or reconstruction, which is typically used on minimally calcified valves. The problem with surgical therapy is the significant risk it imposes on these chronically ill patients with high morbidity and mortality rates associated with surgical repair.

When the native valve is replaced, surgical implantation of the prosthetic valve typically requires an open-chest surgery during which the heart is stopped and patient placed on cardiopulmonary bypass (a so-called "heart-lung machine"). In one common surgical procedure, the diseased native valve leaflets are excised and a prosthetic valve is sutured to the surrounding tissue at the valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective native valves are deemed inoperable because their condition is too frail to withstand the procedure. By some estimates, more than 50% of the subjects suffering from valve stenosis who are older than 80 years cannot be operated on for valve replacement.

Because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For instance, U.S. Pat. Nos. 5,411,522 and 6,730,118, which are incorporated herein by reference, describe collapsible transcatheter heart valves that can be percutaneously introduced in a compressed state on a catheter and expanded in the desired position by balloon inflation or by utilization of a self-expanding frame or stent.

Known prosthetic valves include a frame with a valvular structure (e.g., leaflets) mounted therein, an inner skirt secured to the inside of the frame, and optionally, an outer skirt secured to the exterior of the frame. The inner skirt can serve several functions. For example, the inner skirt can function as a seal member to prevent (or decrease) perivalvular leakage, to anchor the leaflets to the frame, and to protect the leaflets against damage caused by contact with the frame during crimping and during working cycles of the valve. The outer skirt can cooperate with the inner skirt to further reduce or avoid perivalvular leakage after implantation of the valve. The inner skirt desirably is made of a tough, tear resistant material such as polyethylene terephthalate (PET), although various other synthetic or natural materials can be used.

The inner and outer skirts are frequently secured to the frame by suturing or stitching the fabric of the respective skirts to the frame. The leaflets of the prosthetic valve, or at least the cusp edge portions of the leaflets, typically are stitched to the inner skirt of the frame. As can be appreciated, the process of assembling the soft components of a prosthetic valve (e.g., the leaflets and the skirts) to the frame is time-consuming and laborious. Further, the stitching that secures the leaflets to the inner skirt creates stress points on the leaflets, especially during diastole. Accordingly, improvements to skirts for prosthetic valves and methods for their assembly are desirable.

SUMMARY

In a representative embodiment, a method of assembling a prosthetic heart valve comprises securing a suture loop having at least first and second windings to an outflow edge portion of an inner skirt, wherein the first and second windings are arranged in a repeating pattern of figure-eight shape curves and each winding has a plurality of first sections attached to the outflow edge portion of the inner skirt and a plurality of second sections unattached to the inner skirt; placing the inner skirt inside of an annular frame and placing the second sections of the first and second windings over apices of an outflow end of the frame such that the second sections of the first and second windings reside outside of the frame; inserting the second sections of the windings inwardly through openings in the frame; and attaching the second sections of the windings to selected locations on the inner skirt.

In some embodiments, the outflow edge portion of the inner skirt is connected to the frame only by the suture loop.

In some embodiments, the act of securing the suture loop to the outflow edge portion of the inner skirt comprises forming stitches with the first sections of each winding that extend through the outflow edge portion of the inner skirt.

In some embodiments, the act of forming stitches with the first sections of each winding comprises forming in-and-out stitches along adjacent sections of the outflow edge portion of the inner skirt.

In some embodiments, the act of securing the suture loop to the outflow edge portion of the inner skirt comprises attaching the first sections of each winding to the outflow edge portion of the inner skirt with separate sutures.

In some embodiments, the first sections of the first winding alternate with the first sections of the second winding along a length of the suture loop.

In some embodiments, the second sections of the first winding alternate with the second sections of the second winding along a length of the suture loop.

In some embodiments, the method further comprises attaching leaflets to the inner skirt.

In some embodiments, the act of attaching the second sections of the windings to selected locations on the inner skirt comprises securing the second sections of the windings to the selected locations on the inner skirt with sutures.

In another representative embodiment, a method of assembling a prosthetic heart valve comprises providing a skirt having an inflow edge portion and an outflow edge portion; securing a plurality of first sections of a suture loop to one of the inflow edge portion and the outflow edge portion of the skirt; and after securing the suture loop to the skirt, placing the skirt on an annular frame, inserting a plurality of second sections of the suture loop through openings of the frame, and securing the second sections of the suture loop to the skirt.

In some embodiments, the skirt comprises an inner skirt and placing the skirt on the annular frame comprises placing the inner skirt inside of the frame.

In some embodiments, the act of securing the plurality of first sections of the suture loop comprises securing the plurality of first sections to the outflow edge portion of the inner skirt.

In some embodiments, the skirt comprises an outer skirt and placing the skirt on an annular frame comprises placing the outer skirt outside of the frame.

In some embodiments, the suture loop is formed from a single length of suture material.

In some embodiments, the suture loop is formed from only two lengths of suture material.

In some embodiments, the suture loop comprises first and second windings arranged in a repeating pattern of figure-eight shape curves, the plurality of first sections comprises a plurality of first sections of the first winding alternating with a plurality of first sections of the second winding, and the plurality of second sections comprises a plurality of second sections of the first winding alternating with a plurality of second sections of the second winding.

In some embodiments, the method further comprises attaching leaflets to the skirt.

In some embodiments, the act of securing the second sections of the suture loop to the skirt comprises securing the second sections of the suture loop to the skirt with separate sutures.

In another representative embodiment, a prosthetic heart valve comprises an annular frame that is radially expandable from a radially compressed configuration to a radially expanded configuration; an annular skirt having an inflow edge portion and an opposing outflow edge portion; and a suture loop comprising a plurality of first sections secured to one of the inflow edge portion and the outflow edge portion of the skirt and a plurality of second sections extending through openings in the frame and secured to the skirt so as to couple the skirt to the frame.

In some embodiments, the skirt comprises an inner skirt positioned inside of the frame.

In some embodiments, the plurality of first sections of the suture loop are secured to the outflow edge portion of the inner skirt.

In some embodiments, the plurality of first sections of the suture loop are secured to the inflow edge portion of the inner skirt.

In some embodiments, the skirt comprises an outer skirt positioned outside of the frame.

In some embodiments, the plurality of first sections of the suture loop are secured to the outflow edge portion of the outer skirt.

In some embodiments, the plurality of first sections of the suture loop are secured to the inflow edge portion of the outer skirt.

In some embodiments, the prosthetic valve further comprises a plurality of leaflets supported by the skirt.

In some embodiments, the leaflets have cusp edges that are sutured to the skirt.

In some embodiments, the suture loop comprises first and second windings arranged in a repeating pattern of figure-eight shape curves, the plurality of first sections comprises a plurality of first sections of the first winding alternating with a plurality of first sections of the second winding, and the plurality of second sections comprises a plurality of second sections of the first winding alternating with a plurality of second sections of the second winding.

In another representative embodiment, a prosthetic heart valve comprises an annular frame that is radially expandable from a radially compressed configuration to a radially expanded configuration, wherein the frame comprises a plurality of circumferentially extending rows of angled struts connected end-to-end at junctions; an annular skirt having an inflow edge portion and an opposing outflow edge portion; and a suture loop extending along an entire length the outflow edge portion of the skirt and coupling the outflow edge portion of the skirt to one of the rows of struts of the frame without stitching extending around any struts between the junctions of the one row.

In some embodiments, the suture loop comprises a plurality of first sections secured to the outflow edge portion of the skirt and a plurality of second sections extending through openings in the frame and secured to the skirt so as to couple the skirt to the frame.

In some embodiments, the suture loop comprises first and second windings arranged in a repeating pattern of figure-eight shape curves, the plurality of first sections comprises a plurality of first sections of the first winding alternating with a plurality of first sections of the second winding, and the plurality of second sections comprises a plurality of second sections of the first winding alternating with a plurality of second sections of the second winding.

In some embodiments, the first and second windings are formed from a single, continuous piece of suture material.

In some embodiments, the first and second windings are formed from separate pieces of suture material.

In some embodiments, the skirt comprises an inner skirt positioned inside of the frame.

In some embodiments, the skirt comprises an outer skirt positioned outside of the frame.

In some embodiments, the prosthetic heart valve further comprises a plurality of leaflets supported by the skirt.

In some embodiments, the leaflets have cusp edges that are sutured to the skirt.

In some embodiments, the outflow edge portion of the skirt is connected to the frame only by the suture loop.

In another representative embodiment, a prosthetic heart valve comprises an annular frame that is radially expandable from a radially compressed configuration to a radially expanded configuration; an annular inner skirt having an inflow edge portion and an opposing outflow edge portion; a suture loop comprising a plurality of first sections secured to the outflow edge portion of the inner skirt and a plurality of second sections extending through openings in the frame and secured to the inner skirt so as to couple the inner skirt to the frame; and a plurality of leaflets positioned inside of the frame, wherein each leaflet has an inflow end portion that is sutured to the inner skirt.

In some embodiments, the outflow edge portion of the inner skirt is connected to the frame only by the suture loop.

In some embodiments, the first sections of the suture loop form stitches that are stitched to the outflow edge portion of the inner skirt.

In some embodiments, the first sections of the suture loop form in-and-out stitches along adjacent sections of the outflow edge portion of the inner skirt.

In some embodiments, the first sections of the suture loop are secured to the outflow edge portion of the inner skirt with separate sutures.

In some embodiments, the suture loop comprises first and second windings arranged in a repeating pattern of figure-eight shape curves, the plurality of first sections comprises a plurality of first sections of the first winding alternating with a plurality of first sections of the second winding, and the plurality of second sections comprises a plurality of second sections of the first winding alternating with a plurality of second sections of the second winding.

In some embodiments, the leaflets form commissures that are connected to frame.

In some embodiments, the second sections of the suture loop are secured to selected locations on the inner skirt with sutures.

In some embodiments, the frame comprises first and second circumferentially extending rows of angled struts connected end-to-end at junctions and wherein the openings through which the second sections of the suture loop extend are defined by the first and second rows of struts.

In another representative embodiment, a prosthetic heart valve comprises an annular frame that is radially expandable from a radially compressed configuration to a radially expanded configuration; an annular inner skirt having an inflow edge portion and an opposing outflow edge portion; and a suture loop having at least first and second windings secured to an outflow edge portion of an inner skirt, wherein the first and second windings are arranged in a repeating pattern of figure-eight shape curves and each winding has a plurality of first sections attached to the outflow edge portion of the inner skirt and a plurality of second sections extending through openings in the frame and secured to the inner skirt so as to couple the inner skirt to the frame.

In some embodiments, the prosthetic heart valve further comprises a plurality of leaflets positioned inside of the frame, wherein each leaflet has an inflow end portion that is sutured to the inner skirt.

In some embodiments, the leaflets form commissures that are connected to frame.

In some embodiments, the outflow edge portion of the inner skirt is connected to the frame only by the suture loop.

In some embodiments, the first sections of the windings form stitches that are stitched to the outflow edge portion of the inner skirt.

In some embodiments, the first sections of the windings form in-and-out stitches along adjacent sections of the outflow edge portion of the inner skirt.

In some embodiments, the first sections of the windings are secured to the outflow edge portion of the inner skirt with separate sutures.

In some embodiments, the second sections of the windings are secured to selected locations on the inner skirt with sutures.

In some embodiments, the outflow edge portion of the inner skirt has a saw-tooth shape pattern having a plurality of angled sections defining a series of peaks and valleys.

In some embodiments, each first section of the first winding is attached to two adjacent angled sections defining a respective valley and each first section of the second winding is attached to two adjacent angled sections defining a respective valley between angled sections that are attached to respective first sections of the first winding.

The foregoing and other objects, features, and advantages of the invention will become more apparent from the following detailed description, which proceeds with reference to the accompanying figures.

DETAILED DESCRIPTION

Figure 1:
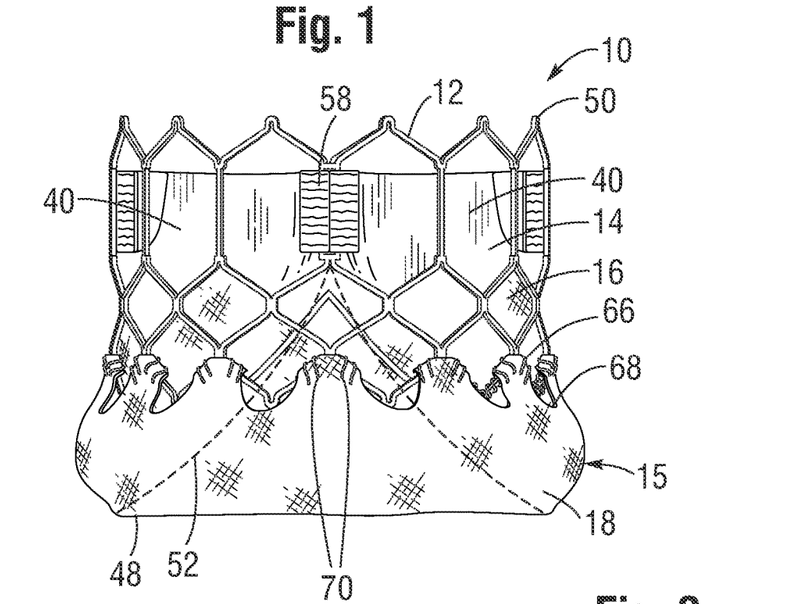
FIG. 1 is a side view of a prosthetic heart valve, according to one embodiment.
Figure 2:
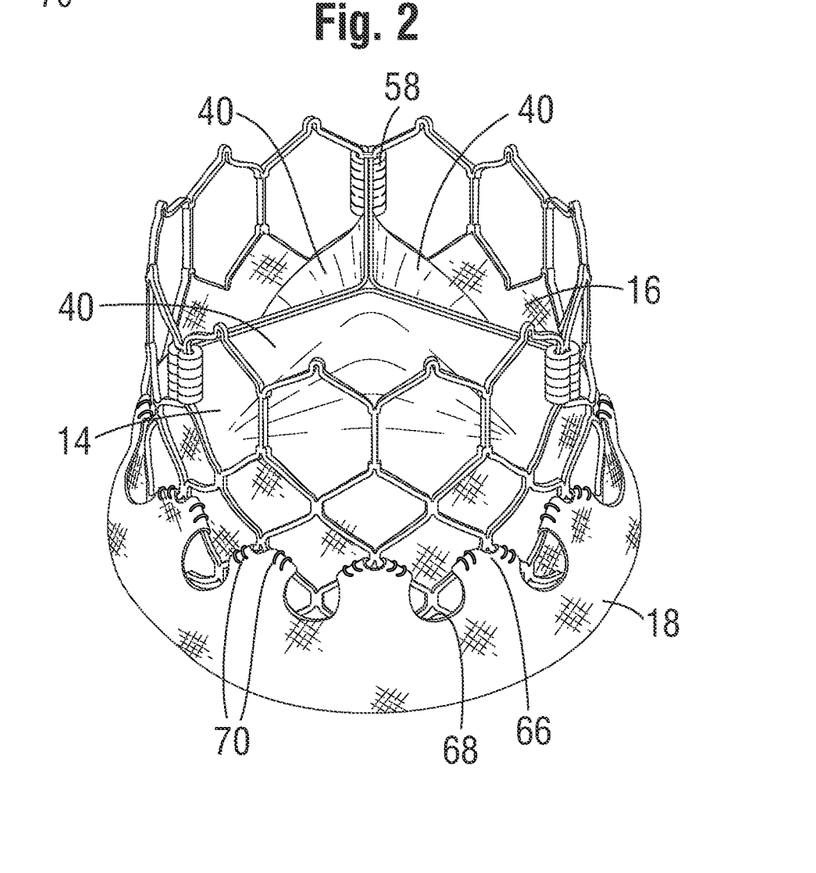
FIG. 2 is a perspective view of the prosthetic heart valve of FIG. 1.

FIGS. 1-2 show two different views of a prosthetic valve 10, according to one embodiment. The illustrated valve is adapted to be implanted in the native aortic annulus, although in other embodiments it can be adapted to be implanted in the other native annuluses of the heart. The valve 10 can have several main components: a stent, or frame, 12, a valvular structure 14, and a skirt assembly 15. The skirt assembly 15 can include an inner skirt 16, and optionally, an outer skirt 18.

The valvular structure 14 (or leaflet structure) can include three leaflets 40 (although a greater or fewer number of leaflets can be used), collectively forming the leaflet structure, which can be arranged to collapse in a tricuspid arrangement. The valvular structure 14 is configured to permit blood to flow through the prosthetic valve 10 in a direction from an inlet end 48 of the prosthetic valve to an outlet end 50 of the prosthetic valve and to block the flow of blood through the prosthetic valve in a direction from the outlet end 50 to the inlet end 48.

Each leaflet 40 desirably has a curved, generally U-shaped inlet or cusp edge 52. In this manner, the inlet edge of the valvular structure 14 has an undulating, curved scalloped shape. By forming the leaflets with this scalloped geometry, stresses on the leaflets can be reduced, which in turn improves durability of the valve. Moreover, by virtue of the scalloped shape, folds and ripples at the belly of each leaflet (the central region of each leaflet), which can cause early calcification in those areas, can be eliminated or at least minimized. The scalloped geometry also reduces the amount of tissue material used to form leaflet structure, thereby allowing a smaller, more even crimped profile at the inflow end of the valve. The leaflets 40 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference herein. Further, the leaflets are configured to permit blood flow from the inflow end to the outflow end, and block blood flow from the outflow end to the inflow end.

Figure 3:
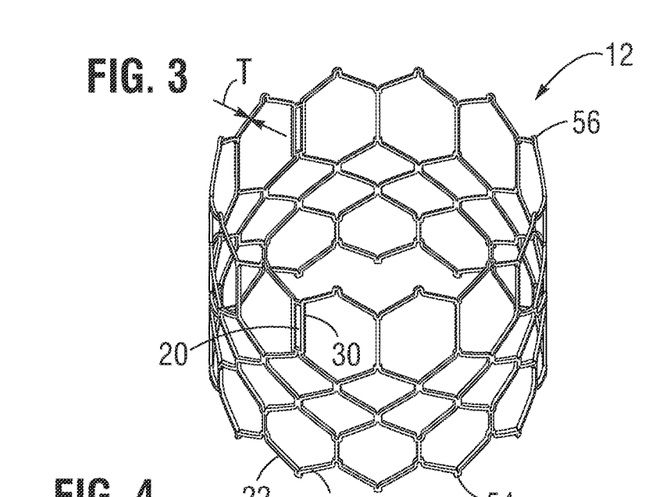
FIG. 3 is a perspective view of the frame of the prosthetic heart valve of FIG. 1.

The bare frame 12 is shown in FIG. 3. In the depicted embodiment, the frame 12 has an annular shape defining an inlet end 54 and an outlet end 56 and includes a plurality of struts (or frame members). The frame 12 can be formed with a plurality of circumferentially spaced slots, or commissure windows, 20 (three in the illustrated embodiment) that are adapted to mount the commissures 58 of the valvular structure 14 to the frame, as described more fully in U.S. Patent Publication No. 2012/0123529, which is incorporated herein by reference.

The frame 12 can be made of any of various suitable plastically-expandable materials (e.g., stainless steel, etc.) or self-expanding materials (e.g., Nitinol) as known in the art. When constructed of a plastically-expandable material, the frame 12 (and thus the valve 10) can be crimped to a radially compressed state on a delivery catheter and then expanded inside a patient by an inflatable balloon or another suitable expansion mechanism. When constructed of a self-expandable material, the frame 12 (and thus the valve 10) can be crimped to a radially compressed state and restrained in the compressed state by insertion into a sheath or equivalent mechanism of a delivery catheter. Once inside the body, the valve can be advanced from the delivery sheath, which allows the valve to expand to its functional size.

Suitable plastically-expandable materials that can be used to form the frame 12 include, without limitation, stainless steel, a nickel based alloy (e.g., a cobalt-chromium or a nickel-cobalt-chromium alloy), polymers, or combinations thereof. In particular embodiments, frame 12 is made of a nickel-cobalt-chromium-molybdenum alloy, such as MP35N™ (tradename of SPS Technologies), which is equivalent to UNS R30035 (covered by ASTM F562-02). MP35N™/UNS R30035 comprises 35% nickel, 35% cobalt, 20% chromium, and 10% molybdenum, by weight. It has been found that the use of MP35N to form frame 12 provides superior structural results over stainless steel. In particular, when MP35N is used as the frame material, less material is needed to achieve the same or better performance in radial and crush force resistance, fatigue resistances, and corrosion resistance. Moreover, since less material is required, the crimped profile of the frame can be reduced, thereby providing a lower profile valve assembly for percutaneous delivery to the treatment location in the body.

Figure 4:
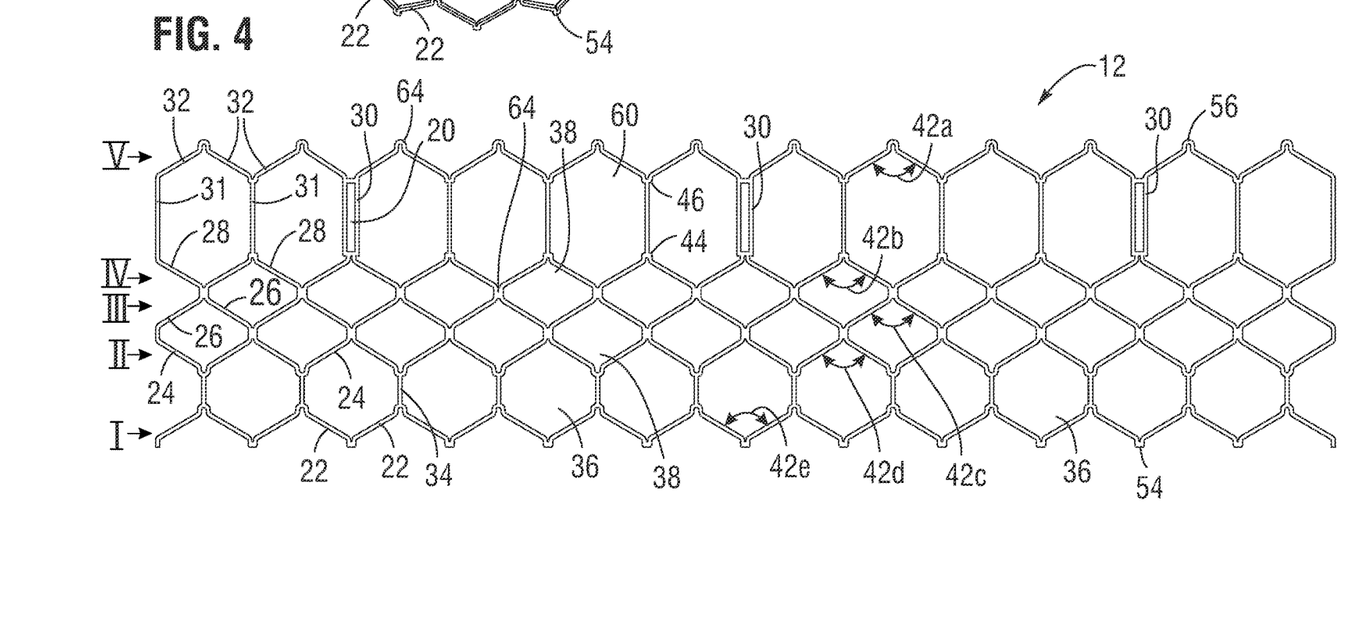
FIG. 4 shows the frame of FIG. 3 in a flattened configuration.

Referring to FIGS. 3 and 4, the frame 12 in the illustrated embodiment includes a first, lower row I of angled struts 22 arranged end-to-end and extending circumferentially at the inflow end of the frame; a second row II of circumferentially extending, angled struts 24; a third row III of circumferentially extending, angled struts 26; a fourth row IV of circumferentially extending, angled struts 28; and a fifth row V of circumferentially extending, angled struts 32 at the outflow end 56 of the frame. A plurality of substantially straight axially extending struts 34 can be used to interconnect the struts 22 of the first row I with the struts 24 of the second row II. The fifth row V of angled struts 32 are connected to the fourth row IV of angled struts 28 by a plurality of axially extending window frame portions 30 (which define the commissure windows 20) and a plurality of axially extending struts 31. Each axial strut 31 and each frame portion 30 extends from a location defined by the convergence of the lower ends of two angled struts 32 to another location defined by the convergence of the upper ends of two angled struts 28.

Each commissure window frame portion 30 mounts a respective commissure 58 of the leaflet structure 14. As can be seen, each frame portion 30 is secured at its upper and lower ends to the adjacent rows of struts to provide a robust configuration that enhances fatigue resistance under cyclic loading of the valve compared to known cantilevered struts for supporting the commissures of the leaflet structure. This configuration enables a reduction in the frame wall thickness to achieve a smaller crimped diameter of the valve. In particular embodiments, the thickness T of the frame 12 (FIG. 3) measured between the inner diameter and outer diameter is about 0.48 mm or less.

The struts and frame portions of the frame collectively define a plurality of open cells of the frame. At the inflow end of the frame 12, struts 22, struts 24, and struts 34 define a lower row of cells defining openings 36. The second, third, and fourth rows of struts 24, 26, and 28 define two intermediate rows of cells defining openings 38. The fourth and fifth rows of struts 28 and 32, along with frame portions 30 and struts 31, define an upper row of cells defining openings 60. The openings 60 are relatively large and are sized to allow portions of the leaflet structure 14 to protrude, or bulge, into and/or through the openings 60 when the frame 12 is crimped in order to minimize the crimping profile.

As shown in FIG. 4, the lower end of the strut 31 is connected to two struts 28 at a node or junction 44, and the upper end of the strut 31 is connected to two struts 32 at a node or junction 46. The strut 31 can have a thickness that is less than the thicknesses of the junctions 44, 46. The junctions 44, 46, along with junctions 64, each of which links two adjacent struts 32, prevent full closure of openings 60 when the frame 12 is in a crimped state. Thus, the geometry of the struts 31, and junctions 44, 46 and 64 assists in creating enough space in openings 60 in the crimped state to allow portions of the leaflets to protrude (i.e., bulge) outwardly through openings. This allows the valve to be crimped to a relatively smaller diameter than if all of the leaflet material is constrained within the crimped frame.

The frame 12 is configured to prevent or at least minimize possible over-expansion of the valve at a predetermined balloon pressure, especially at the outflow end portion of the frame, which supports the leaflet structure 14. In one aspect, the frame is configured to have relatively larger angles 42a, 42b, 42c, 42d, 42e between struts. The larger the angle, the greater the force required to open (expand) the frame. As such, the angles between the struts of the frame can be selected to limit radial expansion of the frame at a given opening pressure (e.g., inflation pressure of the balloon). In particular embodiments, these angles are at least 110 degrees or greater when the frame is expanded to its functional size, and even more particularly these angles are at least 120 degrees or greater when the frame is expanded to its functional size. U.S. Patent Publication No. 2012/0123529 further describes the frame 12 as well as other configurations for frames that can be incorporated in a prosthetic heart valve.

As shown in FIGS. 1-2, the skirt assembly 15 can include an inner skirt 16 that is located inside the frame 12 and an outer skirt 18 that is located outside the frame 12. The inflow (lower) and the outflow (upper) edges of the inner skirt 16 can be secured to the frame 12 and/or the outer skirt 16 by, for example, heat bonding, adhesive, and/or suturing. Typically, the inflow edge is sutured to a respective row of strut, such as the first row I of struts and the outflow edge is sutured to a respective row of struts, such as the third III or fourth IV row of struts. The outer skirt 18 can include a plurality of circumferentially spaced apart extension portions or projections 66 and recesses 68 between adjacent projections formed along the outflow edge (the upper edge in the illustrated embodiment) of the outer skirt. In other embodiments, the outer skirt 18 can have a straight outflow edge without any projections or recesses.

The inflow (lower) and the outflow (upper) edges of the outer skirt 18 can be secured to the frame 12 and/or the inner skirt 16 by, for example, heat bonding, adhesive, and/or suturing. As shown in the illustrated embodiment, the projections 66 along the outflow edge of the outer skirt 18 can be secured to struts of the frame with sutures 70 while the recesses 68 between adjacent projections can be left unattached to the frame 12 and the inner skirt 16. The outer skirt 18 functions as a sealing member for the prosthetic valve 10 by sealing against the tissue of the native valve annulus, helping to reduce paravalvular leakage past the prosthetic valve 10.

In some embodiments, as shown in FIGS. 1-2, the outer skirt 18 can be configured to extend radially outward from the frame 12 when the prosthetic valve 10 is in a radially expanded configuration. Alternatively, the outer skirt 18 can be configured to form a snug fit with the frame 12 such that it lies against the outer surface of the frame 12 when the prosthetic valve 10 is in the radially expanded configuration, such as disclosed in WIPO Publication No. 2018/222799, which is incorporated herein by reference. The outer skirt 18 can be formed from any of various synthetic materials or natural tissue (e.g., pericardial tissue). Suitable synthetic materials include any of various biocompatible fabrics (e.g., PET fabric) or non-fabric films, including any of the materials disclosed below for the reinforcing layer 88 of the inner skirt 16. Further details of the outer skirt 18 are also disclosed in U.S. Patent Publication No. 2012/0123529 and WIPO Publication No. 2018/222799.

As further shown in FIGS. 1-2, the inner skirt 16 in the illustrated embodiment extends from the inlet end 54 of the frame to the fourth row IV of angled struts 28. In other embodiments, the inner skirt 16 can extend from the inlet end 54 of the frame to a location short of the fourth row IV of struts (e.g., to the second row II or the third row III of struts), or the inner skirt can extend the entire height of the frame 12 (e.g., from the inlet end 54 to the outlet end 56). In alternative embodiments, the inner skirt 16 can be positioned and/or sized to extend over a different portion of the frame 12 than the configuration shown in FIGS. 1-2. For example, in some embodiments, the inflow end of the inner skirt 16 can be axially spaced from the inlet end 54 of the frame 12.

Although the inner skirt 16 is typically tubular or cylindrical in shape (forming a complete circle in a cross-sectional profile in a plane perpendicular to the longitudinal axis of the valve), the inner skirt 16 need not extend along the inner surface of the frame 12 in the circumferential direction through 360 degrees. In other words, the inner skirt 16 can have a cross-sectional profile (in a plane perpendicular to the axis of the lumen of the valve) that is not a complete circle. The inner skirt 16 can be initially formed as a flat strip, and then formed to the annular shape by coupling together opposing edge portions, for example, by sewing, thermal bonding, and/or adhesive. Alternatively, the inner skirt 16 can be formed directly in an annular shape, for example, by constructing the inner layer 16 on a cylindrically shaped mandrel as described below.

As noted above, the leaflets 40 can be secured to one another at their adjacent sides to form commissures 58. Each commissure 58 can be secured to a corresponding commissure window 20 of the frame 12, as described in U.S. Patent Publication No. 2012/0123529. The inflow or cusp edges 52 of the leaflets 40 can be sutured to the inner skirt 16 along a suture line that tracks the curvature of the scalloped inflow edge of the leaflet structure.

In some embodiments, the inflow edges 52 of the leaflets 40 are secured to the inner skirt 16 prior to mounting the inner skirt 16 to the frame. After securing the leaflets 40 to the inner skirt 16, the inner skirt is then secured to the frame as described above and the commissures 58 of the leaflets are mounted to the frame. In other embodiments, the inner skirt 16 can be mounted to the frame without the leaflets, after which the inflow edges 52 of the leaflets are then secured to the inner skirt.

In certain embodiments, the inflow edges 52 of the leaflets 40 can be secured to the inner skirt via a thin PET reinforcing strip (not shown), as disclosed in U.S. Pat. No. 7,993,394, which is incorporated herein by reference. As described in U.S. Pat. No. 7,993,394, the reinforcing strip can be sutured to the inflow edges of the leaflets. The reinforcing strip and the lower edges of the leaflets can then be sutured to the inner skirt 16. The reinforcing strip desirably is secured to the inner surfaces of the leaflets 40 such that the inflow edges 52 of the leaflets become sandwiched between the reinforcing strip and the inner skirt when the leaflets and the reinforcing strip are secured to the inner skirt. The reinforcing strip enables a secure suturing and protects the pericardial tissue of the leaflet structure from tears.

FIGS. 5-8 illustrate an alternative technique for mounting the soft components of a prosthetic valve (e.g., the inner skirt 16, the outer skirt 18, and/or the leaflets 40) to a frame of the prosthetic valve. The depicted embodiment illustrates a method of mounting the inner skirt 16 and the leaflets 40 to a frame 120. The frame 120 has an inflow end 122 and an outflow end 124. The frame in the illustrated embodiment comprises a plurality of circumferentially extending rows of struts, including a first row I of angled struts 126, a second row II of angled struts 128, a third row III of angled struts 130, a fourth row IV of angled struts 132. The struts 132 form a plurality of apices 134 at the outflow end 124 of the frame. In other embodiments, the frame 120 can have a greater or fewer number of rows of struts.

Figure 6:
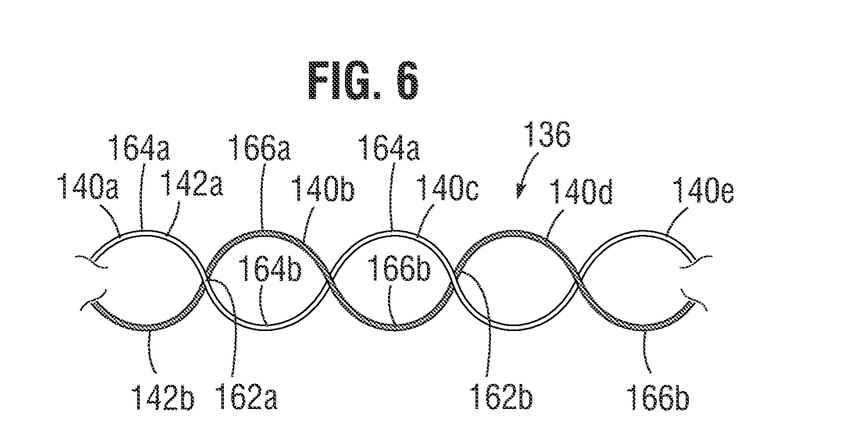

An exemplary method of assembling the skirt 16 onto the frame 120 includes securing a main suture loop 136 to an outflow edge portion 138 of the inner skirt 16. The outflow edge portion 138 of the inner skirt 16 can have an undulating or saw-tooth shaped pattern defining a series of peaks and valleys that correspond to the shape of the third row III of struts 130. As best shown in FIG. 6, the suture loop 136 in the illustrated embodiment is configured as a repeating pattern of figure-eight shaped curves arrayed end-to-end so as to form a series or two or more sub-loops 140a, 140b, 140c, 140d, 140e along the length of the main loop 136. The number of sub-loops 140a-e desirably equals the number of apices 134 at the outflow end 124 of the frame 120. In one example, the frame 120 has 12 apices 134 (similar to frame 12) and 12 sub-loops 140a-e. However, the number of sub-loops can vary depending on the particular application.

The suture loop 136 in the illustrated embodiment has at least first and second windings 142a, 142b, respectively, that form respective sinusoidal curves. The curves are offset or displaced from each other by one-half of a "wavelength" (a full wavelength being the length of a winding 142a, 142b from a first location 162a where the windings intersect to a second location 162b where the windings intersect). In this manner, the first winding 142a has a plurality of half-wavelength sections 164a that curve in one direction alternating with a plurality of half-wavelength sections 164b that curve in the opposite direction. Similarly, the second winding 142b has a plurality of half-wavelength sections 166a that curve in one direction alternating with a plurality of half-wavelength sections 166b that curved in the opposite direction. Each section 164a is paired with a corresponding section 166b and each section 164b is paired with a corresponding section 166a to form the sub-loops 140a-e.

The suture loop 136 can be formed from any of various types and sizes of sutures, including any of various single filament or multi-filament sutures. In particular embodiments, for example, the suture loop 136 is made of a 2-0 or 3-0 size suture, such as a Dyneema or Ethibond suture. In some embodiments, the suture loop 136 can be made of braided or twisted multi-filament suture material.

Figure 5:
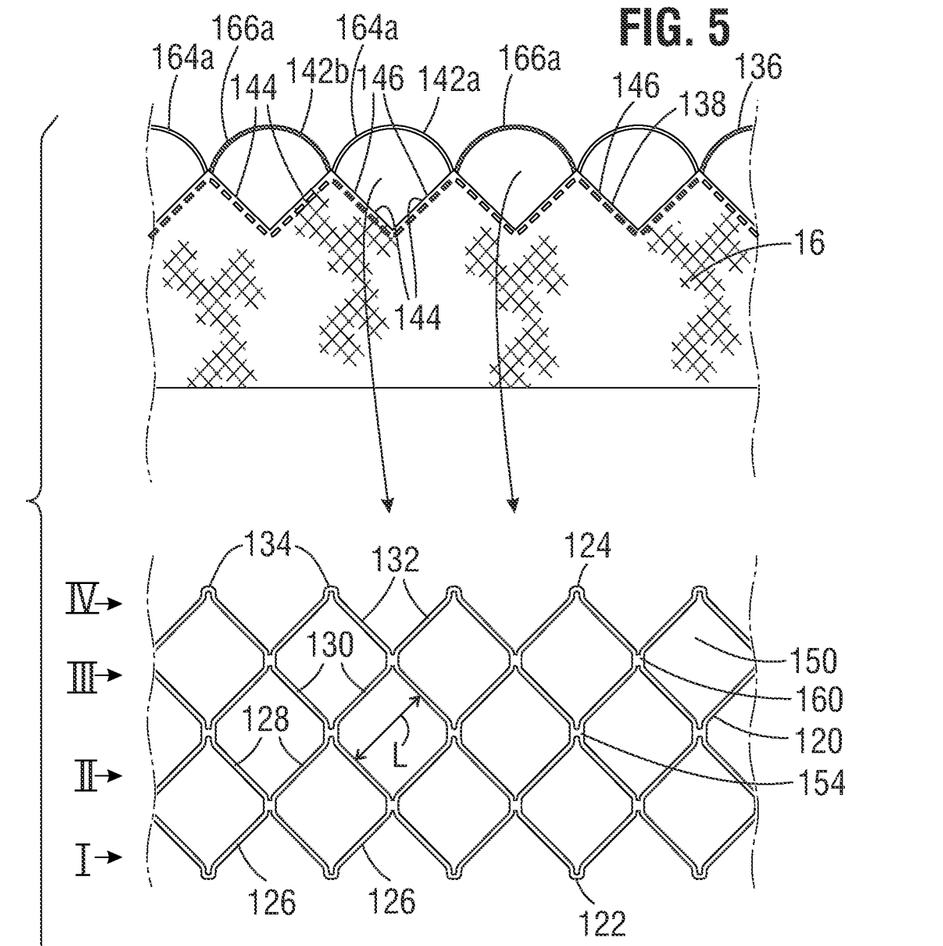
FIGS. 5-8 shows a method of mounting an inner skirt on a frame of a prosthetic heart valve, according to one embodiment.

In one embodiment, the main suture loop 136 is formed into the repeating figure-eight pattern shown in FIGS. 5-6 as it is secured to the outflow edge portion 138 of the skirt 16. This can be accomplished by taking a single length of suture and securing the first winding 142a of the suture in intervals along the outflow edge portion 138. In particular, the first winding 142a is secured to every pair of adjacent sections 144 of the outflow edge portion 138, such as by forming in-and-out stitches along the sections 144, while skipping each pair of adjacent sections 146 located between sections 144 such that winding sections 164b are attached to the skirt sections 144 and sections 164a are not attached to the skirt.

After the first winding 142a is secured along the entire length of the outflow edge portion 138 (skipping pairs of adjacent sections 146), the second winding 142b of the suture is secured to every pair of adjacent skirt sections 146, such as by forming in-and-out stitches along the sections 146, while skipping each pair of adjacent sections 144 located between sections 146 such that winding sections 166b are attached to the skirt sections 146 and winding sections 166a are not attached to the skirt. In this manner, the first and second windings 142a, 142b form the repeating figure-eight pattern defining the plurality of sub-loops 140a-e as shown in FIG. 6. Thereafter, the ends of the suture can be tied off or otherwise secured to each other to form a continuous loop. In other embodiments, the ends of the suture need not be connected to each other to form a continuous loop and instead can be tied or otherwise secured to struts of the frame when the inner skirt 16 is later placed on the frame. The skirt 16 desirably is in a flattened (non-cylindrical) configuration when the main suture loop 136 is secured to the skirt to facilitate the stitching process.

In an alternative embodiment, the main suture loop 136 can be formed using two separate pieces or lengths of suture. A first length of suture can be secured to skirt sections 144 as described above to form the first winding 142a and a separate, second length of suture can be secured to sections 146 as described above to form the second winding 142b. The adjacent ends of the first and second lengths of suture can be tied off or otherwise secured to each other to form a continuous loop. In other embodiments, the adjacent ends of the windings 142a, 142b need not be connected to each other to form a continuous loop and instead can be tied or otherwise secured to struts of the frame when the inner skirt 16 is later placed on the frame.

When forming the main suture loop 136, each section 164a, 164b of the first winding 142a and each section 166a, 166b of the second winding 142b desirably has an overall length equal to or approximately equal to twice the length L of a strut 130. This allows the unattached sections 164a, 166a of the windings 142a, 142b to be later secured to the skirt at locations adjacent the junctions of the third row III of struts 130, as further described in greater detail below.

Figure 7:
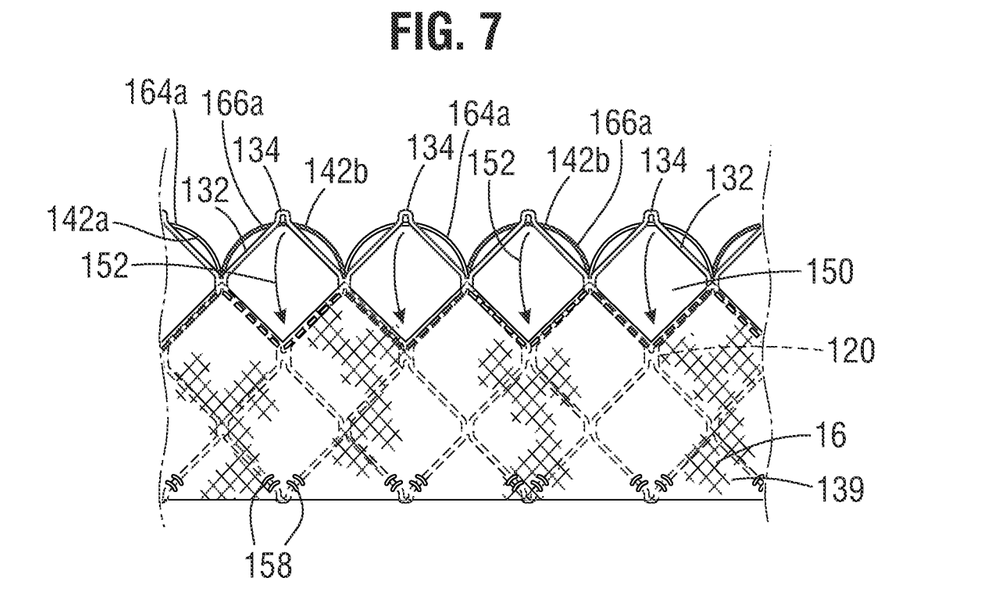

Referring now to FIG. 7, after securing the main suture loop 136 to the skirt 16, the skirt can be placed inside of the frame 120 with the unattached sections 164a, 166a of the windings 142a, 142b placed over the apices 134 at the outflow end of the frame. When the outflow edge portion 138 is aligned with the struts 130 of the third row III, the unattached sections 164a, 166a of the windings 142a, 142b extend behind struts 132 of the fourth row IV on the outside of the frame 120. The unattached sections 164a, 166a of the windings 142a, 142b can then be inserted inwardly into the interior of the frame through the cell openings 150 defined between the third and fourth rows of struts, as indicated by arrows 152 (e.g., by pushing or pulling the sections 164a, 166a through the cell openings 150).

Figure 8:
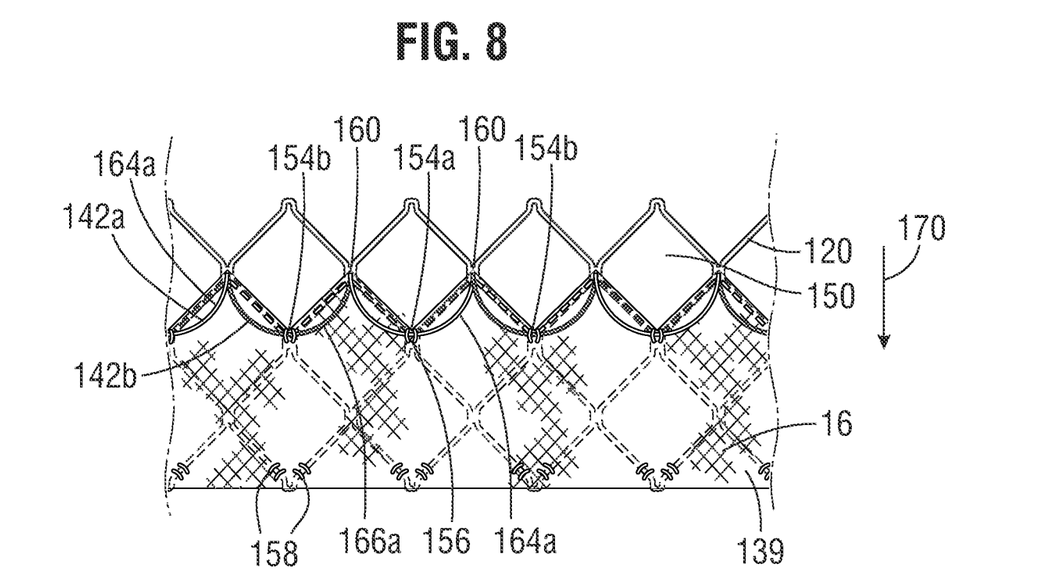

The unattached sections 164a, 166a of the windings 142a, 142b can now be attached to the inner skirt 16 at selected locations. For example, as shown in FIG. 8, the unattached sections 164a, 166a can be attached to the outflow edge portion 138 at locations adjacent frame junctions 154 between the second and third rows of struts. In particular, each section 164a can be attached to the outflow edge portion 138 adjacent a respective junction 154a and each section 166a can be attached to the outflow edge portion 138 adjacent respective junctions 154b. Sections 164a, 166a of the windings can be attached to the outflow edge portion 138 using separate sutures 156 at each junction 154a, 154b. Each suture 156 can form one or more stitches that extends through the skirt material and around the adjacent winding section 164a, 166a. The inflow edge portion 139 of the skirt 16 can be secured to the skirt using conventional techniques, such as by stitching the skirt to the first row I of struts 126 with sutures 158.

It should be noted that the previously unattached sections 164a, 166a of the windings 142a, 142b pulled into the interior of the frame are depicted in FIG. 8 as being slightly longer than corresponding attached sections 164b, 166b of the windings 142a, 142b for purposes of illustration. However, these sections desirably have equal lengths. Thus, once secured with sutures 158, the sections 164a, 166a can track or correspond to the shape of the outflow edge portion 138 of the skirt and the stitching formed by the sections 164b, 166b.

Figure 9A:
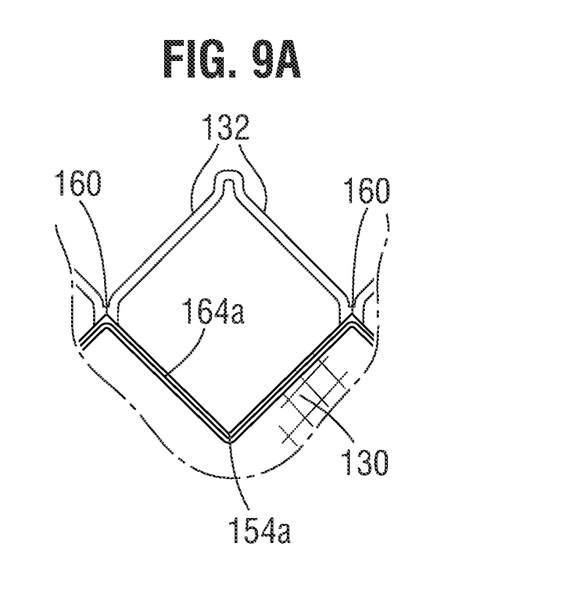
FIGS. 9A and 9B are enlarged views of a cell of the frame in the radially expanded configuration and the radially compressed configuration, respectively.
Figure 9B:
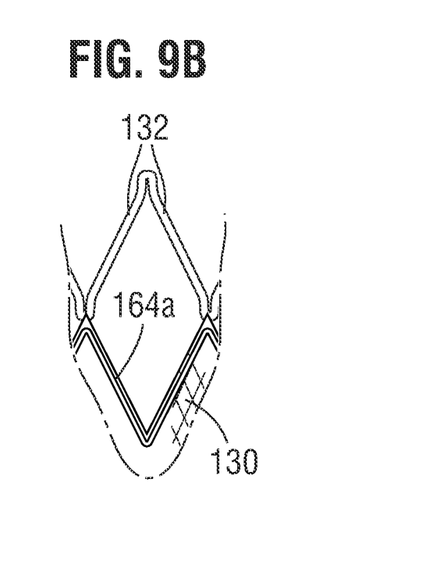

FIGS. 9A and 9B shows a representative frame cell of the uppermost row of cells of the frame (the cells formed by the third row of struts 130 and the fourth row of struts 132) when the frame 120 is in the radially expanded configuration (FIG. 9A) and radially compressed configuration (FIG. 9B). As shown, the height of the cell in the axial direction decreases when the frame is radially expanded and increases when the frame is radially compressed. As noted above, each section 164a, 164b of the first winding 142a and each section 166a, 166b of the second winding 142b desirably has an overall length equal to or approximately equal to twice the length L of a strut 130. This accommodates foreshortening of the frame cells when the prosthetic valve is radially expanded.

After the inner skirt 16 is mounted to the frame 120, a valvular structure, such as a plurality of leaflets 40, can be mounted to the inner skirt 16 and/or the frame 120. For example, the cusp (inflow) edges of the leaflets 40 can be sutured to the inner skirt 16 and the commissures of the leaflets can be sutured to the inner skirt and/or adjacent cells of the frame. In alternative embodiments, the cusp edges of the leaflets 40 can be secured (e.g., sutured) to the skirt 16 prior to assembling the inner skirt on the frame. The commissures of the leaflets 40 can be secured to cells of the frame after placing the inner skirt and the leaflets inside of the frame. Further details regarding the assembly of the leaflets 40 to the inner skirt and the frame are disclosed in U.S. Patent Publication Nos. 2010/0049313, 2012/0123529, and 2018/0028310, which are incorporated herein by reference.

In particular embodiments, the sutures 156 used to attach the windings 142a, 142b to the skirt do not secure the outflow edge portion 138 of the skirt directly to the frame 120. In other words, in such embodiments, the sutures 156 do not extend around any of the struts of the frame. In particular embodiments, in contrast to known prosthetic valves, no stitching is used to secure the outflow edge portion of the inner skirt to the struts of the frame. Instead, in such embodiments, the outflow edge portion 138 is secured or connected indirectly to the frame only by the main suture loop 136 that extends into and out of the frame at frame junctions 160 between the third and fourth rows of struts and need not include any stitching looping around the struts 130 between junctions 154 and 160. In this manner, the outflow edge portion 138 of the inner skirt 16 is suspended from the frame 120 by the main suture loop 136. During diastole, the leaflets 40 close under pressure from the flow of retrograde blood (in the direction of arrow 170 in FIG. 8). The diastolic load is transferred from the leaflets to the inner skirt to the frame via the main suture loop 136. In this manner, most of the forces acting on the prosthetic valve during diastole are born by the metal struts of the frame and not the leaflets, which are more susceptible of wear and tear. Thus, as can be appreciated, the disclosed methods and configurations can improve long term wearability and performance of the prosthetic valve.

Moreover, in known prosthetic valves, the outflow edge portion of the inner skirt typically is secured to the frame with stitching that secures the outflow edge portion of the inner skirt to an entire row of struts of the frame, which is a time-consuming and laborious process. The disclosed methods greatly facilitate the assembly process because no stitching is needed to secure the outflow edge portion of the inner skirt directly to the struts of the frame.

Figure 10:
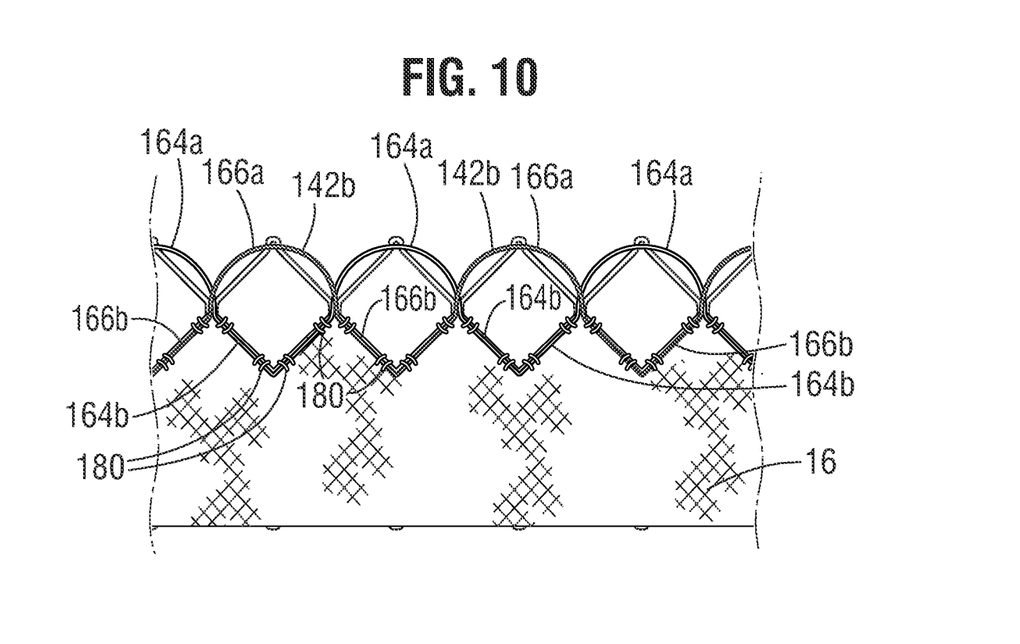
FIG. 10 shows an alternative method of mounting a suture loop to an inner skirt for mounting the inner skirt on a frame.

FIG. 10 shows an alternative way of securing the main suture loop 136 to the inner skirt 16. In this embodiment, the windings 142a, 142b are laid out against one side of the inner skirt as shown in FIG. 10 such that sections 164b and 166b of the first and second windings extend along the outflow edge portion 138. The winding sections 164b, 166b are then secured to the outflow edge portion 138 using suitable techniques or mechanisms. For example, the winding sections can be secured to the inner skirt 16 with stiches 180 placed at selected locations along the outflow edge portion. For example, as shown in FIG. 10, the sutures 180 can be placed near the valleys and peaks of the outflow edge portion 138 of the inner skirt. After securing the main suture loop 136 to the inner skirt 16, the inner skirt 16 can be placed on and secured to the frame as previously described above in connection with FIGS. 5-8. Further, a valvular structure, such as a plurality of leaflets 40, can be mounted to the inner skirt 16 and/or the frame 120 as previously described.

In the embodiments described above, the main suture loop 136 has first and second windings 142a, 142b. In alternative embodiments, a main suture loop 136 can have more than two windings, such as three, four or more windings.

In the methods described above, a main suture loop 136 is used to secure the outflow edge portion 138 of the inner skirt 16 to the frame 120. However, in other embodiments, the same methods can be used to secure the inflow edge portion 139 of the inner skirt 16 to the frame. For example, another main suture loop 136 can be secured to the inflow edge portion 139 of the inner skirt (such as shown in FIG. 5 or FIG. 10 for the outflow edge portion 138) and then secured to the inflow end of the frame (similar to FIGS. 5-8 but placing the sub-loops 140a-e around the apices at the inflow end 122 of the frame). In some embodiments, the inflow edge portion 139 of the skirt 16 can be shaped similar to the outflow edge portion 138 such that it has a series of peaks and valleys that follow the shape of the first row I of struts 126 to facilitate placement of the sub-loops 140a-e around the apices at the inflow end 122 of the frame.

In alternative embodiments, the methods of assembling the inner skirt 16 to the frame 120 disclosed herein also can be used to assemble an outer skirt (e.g., outer skirt 18) to the frame of a prosthetic valve. For example, a main suture loop 136 can be secured to the outflow edge portion of an outer skirt and the outer skirt can be secured to the frame 120 as described above in connection with FIGS. 5-8, except that the outer skirt is placed on the outside of the frame and the sub-loops 140a-e are placed over the apices 134 such that unattached sections of the windings are inside of the frame. The unattached sections of the windings can then be pulled outwardly through the openings 150 of the frame 120 and then attached to the outer skirt, such as with sutures (similar to sutures 156). In further embodiments, the inflow edge portion of an outer skirt can be mounted to a frame with a suture loop 136, or the inflow edge portion and the outflow edge portion of an outer skirt can be mounted to a frame with respective suture loops 136.

General Considerations

It should be understood that the disclosed embodiments can be adapted to deliver and implant prosthetic devices in any of the native annuluses of the heart (e.g., the aortic, pulmonary, mitral, and tricuspid annuluses), and can be used with any of various delivery approaches (e.g., retrograde, antegrade, transseptal, transventricular, transatrial, etc.).

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved. The technologies from any example can be combined with the technologies described in any one or more of the other examples. In view of the many possible embodiments to which the principles of the disclosed technology may be applied, it should be recognized that the illustrated embodiments are only preferred examples and should not be taken as limiting the scope of the disclosed technology.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods.

These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "connected" generally mean electrically, electromagnetically, and/or physically (e.g., mechanically or chemically) coupled or linked and does not exclude the presence of intermediate elements between the coupled or associated items absent specific contrary language.

Directions and other relative references (e.g., inner, outer, upper, lower, etc.) may be used to facilitate discussion of the drawings and principles herein, but are not intended to be limiting. For example, certain terms may be used such as "inside," "outside,", "top," "down," "interior," "exterior," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same. As used herein, "and/or" means "and" or "or", as well as "and" and "or".

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. I therefore claim as my invention all that comes within the scope and spirit of these claims.

We claim:

1. A method of assembling a prosthetic heart valve comprising:
    securing a suture loop having at least first and second windings to an outflow edge portion of an inner skirt, wherein the first and second windings are arranged in a repeating pattern of figure-eight shape curves and each winding has a plurality of first sections attached to the outflow edge portion of the inner skirt and a plurality of second sections unattached to the inner skirt;
    after securing the suture loop to the inner skirt, placing the inner skirt inside of an annular frame and placing the second sections of the first and second windings over apices of an outflow end of the frame such that the second sections of the first and second windings reside outside of the frame;
    inserting the second sections of the windings inwardly through openings in the frame; and
    attaching the second sections of the windings to selected locations on the inner skirt.

2. The method of claim 1, wherein the outflow edge portion of the inner skirt is connected to the frame only by the suture loop.

3. The method of claim 1, wherein securing the suture loop to the outflow edge portion of the inner skirt comprises forming stitches with the first sections of each winding that extend through the outflow edge portion of the inner skirt.

4. The method of claim 3, wherein forming stitches with the first sections of each winding comprises forming in-and-out stitches along adjacent sections of the outflow edge portion of the inner skirt.

5. The method of claim 1, wherein securing the suture loop to the outflow edge portion of the inner skirt comprises attaching the first sections of each winding to the outflow edge portion of the inner skirt with separate sutures.

6. The method of claim 1, wherein the first sections of the first winding alternate with the first sections of the second winding along a length of the suture loop.

7. The method of claim 1, wherein the second sections of the first winding alternate with the second sections of the second winding along a length of the suture loop.

8. The method of claim 1, further comprising attaching leaflets to the inner skirt.

9. The method of claim 1, wherein attaching the second sections of the windings to selected locations on the inner skirt comprises securing the second sections of the windings to the selected locations on the inner skirt with sutures.

10. A method of assembling a prosthetic heart valve comprising:
    providing a skirt having an inflow edge portion and an outflow edge portion;
    securing a plurality of first sections of a suture loop to one of the inflow edge portion and the outflow edge portion of the skirt, wherein a plurality of second sections of the suture loop are unattached to the inner skirt; and
    after securing the plurality of first sections of the suture loop to the skirt, placing the skirt on an annular frame, inserting the plurality of second sections of the suture loop through openings of the frame, and securing the second sections of the suture loop to the skirt.

11. The method of claim 10, wherein the skirt comprises an inner skirt and placing the skirt on the annular frame comprises placing the inner skirt inside of the frame.

12. The method of claim 11, wherein the act of securing the plurality of first sections of the suture loop comprises securing the plurality of first sections to the outflow edge portion of the inner skirt.

13. The method of claim 10, wherein the skirt comprises an outer skirt and placing the skirt on an annular frame comprises placing the outer skirt outside of the frame.

14. The method of claim 10, wherein the suture loop is formed from a single length of suture material.

15. The method of claim 10, wherein the suture loop is formed from only two lengths of suture material.

16. The method of claim 10, wherein the suture loop comprises first and second windings arranged in a repeating pattern of figure-eight shape curves, the plurality of first sections comprises a plurality of first sections of the first winding alternating with a plurality of first sections of the second winding, and the plurality of second sections comprises a plurality of second sections of the first winding alternating with a plurality of second sections of the second winding.

17. The method of claim 10, further comprising attaching leaflets to the skirt.

18. The method of claim 10, wherein the act of securing the second sections of the suture loop to the skirt comprises securing the second sections of the suture loop to the skirt with separate sutures.

19. A prosthetic heart valve comprising:
    an annular frame that is radially expandable from a radially compressed configuration to a radially expanded configuration;

an annular skirt having an inflow edge portion and an opposing outflow edge portion; and a suture loop comprising a plurality of first sections secured to one of the inflow edge portion and the outflow edge portion of the skirt and a plurality of second sections extending through openings in the frame and secured to the skirt so as to couple the skirt to the frame, wherein each first section forms a plurality of stitches along the skirt without extending around any portion of the frame and each second section extends from an end of one of the first sections to an end of another one of the first sections without extending through the skirt, wherein each second section is secured to the skirt using a separate suture that forms one or more stitches that extend through the skirt material and around the second section.

20. The prosthetic heart valve of claim 19, wherein the suture loop comprises first and second windings arranged in a repeating pattern of figure-eight shape curves, the plurality of first sections comprises a plurality of first sections of the first winding alternating with a plurality of first sections of the second winding, and the plurality of second sections comprises a plurality of second sections of the first winding alternating with a plurality of second sections of the second winding.

* * * * *